(12) United States Patent
Patterson et al.

(10) Patent No.: US 7,766,942 B2
(45) Date of Patent: Aug. 3, 2010

(54) POLYMER RODS FOR SPINAL APPLICATIONS

(75) Inventors: Christopher M. Patterson, Olive Branch, MS (US); Thomas Carls, Memphis, TN (US); Fred J. Molz, IV, Birmingham, AL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 298 days.

(21) Appl. No.: 11/469,354

(22) Filed: Aug. 31, 2006

(65) Prior Publication Data

US 2008/0086127 A1 Apr. 10, 2008

(51) Int. Cl.
*A61B 17/70* (2006.01)

(52) U.S. Cl. .................. 606/261; 606/254

(58) Field of Classification Search ............ 132/247, 132/273, 275; 606/260–261, 250–255; 403/105
See application file for complete search history.

(56) References Cited

U.S. PATENT DOCUMENTS

| | | | | |
|---|---|---|---|---|
| 4,633,864 A | * | 1/1987 | Walsh | 128/207.15 |
| 5,059,193 A | * | 10/1991 | Kuslich | 606/247 |
| 5,133,716 A | * | 7/1992 | Plaza | 606/250 |
| 5,154,718 A | * | 10/1992 | Cozad et al. | 606/252 |
| 5,217,461 A | | 6/1993 | Asher et al. | |
| 5,257,974 A | * | 11/1993 | Cox | 604/103.05 |
| 5,415,661 A | | 5/1995 | Holmes | |
| 5,486,174 A | | 1/1996 | Fournet-Fayard et al. | |
| 5,591,164 A | | 1/1997 | Nazre et al. | |
| 5,593,408 A | | 1/1997 | Gayet et al. | |
| 5,845,454 A | * | 12/1998 | Malizia | 52/713 |
| 5,893,889 A | | 4/1999 | Harrington | |
| 5,997,542 A | | 12/1999 | Burke | |
| 6,093,188 A | | 7/2000 | Murray | |
| 6,099,528 A | | 8/2000 | Saurat | |

(Continued)

FOREIGN PATENT DOCUMENTS

FR 2799949 4/2001

(Continued)

OTHER PUBLICATIONS

Wang, A., et al. "Carbon Fiber Reinforced Polyether Ether Ketone Composite as a Bearing Surface for Total Hip Replacement," Tribolology International, vol. 31, No. 11, pp. 661-667 (1998).

(Continued)

*Primary Examiner*—Eduardo C Robert
*Assistant Examiner*—Julianna N Harvey

(57) ABSTRACT

A method of manufacturing a curved spinal rod is disclosed. The method includes heating PEEK; injecting the PEEK into an arcuate spinal rod mold; holding the injected PEEK in the mold until the PEEK substantially sets; and removing the injected PEEK from the mold. In another aspect, a spinal rod is disclosed. The spinal rod includes an arcuate main body having a first end portion, a second end portion, and a central portion. The central portion has a non-circular cross-section with a height greater than its width. The first and second end portions and the central portion of the arcuate main body are integrally formed of a polymer such as polyetheretherketone (PEEK). The spinal rod also includes a rounded end cap adapted to mate with at least one of the end portions. The end cap is radiopaque.

25 Claims, 7 Drawing Sheets

U.S. PATENT DOCUMENTS

| | | | |
|---|---|---|---|
| 6,102,912 A | 8/2000 | Cazin et al. | |
| 6,206,882 B1 | 3/2001 | Cohen | |
| 6,267,764 B1 | 7/2001 | Elberg | |
| 6,610,062 B2 * | 8/2003 | Bailey et al. | 606/261 |
| 6,652,530 B2 | 11/2003 | Ip et al. | |
| 6,733,531 B1 | 5/2004 | Trieu | |
| 6,786,930 B2 | 9/2004 | Biscup | |
| 6,966,910 B2 | 11/2005 | Ritland | |
| 6,986,771 B2 | 1/2006 | Paul et al. | |
| 6,989,011 B2 | 1/2006 | Paul et al. | |
| 2003/0171749 A1 | 9/2003 | Le Couedic et al. | |
| 2004/0002708 A1 | 1/2004 | Ritland | |
| 2004/0049189 A1 | 3/2004 | Le Couedic et al. | |
| 2004/0102777 A1 | 5/2004 | Huebner | |
| 2004/0147928 A1 | 7/2004 | Landry et al. | |
| 2004/0243241 A1 | 12/2004 | Istephanous et al. | |
| 2004/0260287 A1 * | 12/2004 | Ferree | 606/61 |
| 2004/0267260 A1 | 12/2004 | Mack et al. | |
| 2005/0038432 A1 * | 2/2005 | Shaolian et al. | 606/61 |
| 2005/0065515 A1 | 3/2005 | Jahng | |
| 2005/0065516 A1 | 3/2005 | Jahng | |
| 2005/0085815 A1 | 4/2005 | Harms et al. | |
| 2005/0090821 A1 * | 4/2005 | Berrevoets et al. | 606/61 |
| 2005/0124991 A1 | 6/2005 | Jahng | |
| 2005/0131405 A1 | 6/2005 | Molz et al. | |
| 2005/0143823 A1 | 6/2005 | Boyd et al. | |
| 2005/0149020 A1 | 7/2005 | Jahng | |
| 2005/0154390 A1 | 7/2005 | Biedermann et al. | |
| 2005/0171539 A1 | 8/2005 | Braun et al. | |
| 2005/0171540 A1 | 8/2005 | Lim et al. | |
| 2005/0177157 A1 | 8/2005 | Jahng | |
| 2005/0203511 A1 | 9/2005 | Wilson-MacDonald et al. | |
| 2005/0203513 A1 | 9/2005 | Jahng et al. | |
| 2005/0203514 A1 | 9/2005 | Jahng et al. | |
| 2005/0203517 A1 | 9/2005 | Jahng et al. | |
| 2005/0203518 A1 | 9/2005 | Biedermann et al. | |
| 2005/0203519 A1 | 9/2005 | Harms et al. | |
| 2005/0209593 A1 | 9/2005 | Kolb | |
| 2005/0209694 A1 | 9/2005 | Loeb | |
| 2005/0261686 A1 | 11/2005 | Paul | |
| 2005/0267471 A1 | 12/2005 | Biedermann et al. | |
| 2005/0277922 A1 | 12/2005 | Trieu et al. | |
| 2005/0277926 A1 | 12/2005 | Farris | |
| 2005/0277932 A1 | 12/2005 | Farris | |
| 2006/0009768 A1 | 1/2006 | Ritland | |
| 2006/0041259 A1 | 2/2006 | Paul et al. | |
| 2006/0064090 A1 | 3/2006 | Park | |
| 2006/0079953 A1 | 4/2006 | Gregorich et al. | |
| 2006/0084982 A1 | 4/2006 | Kim | |
| 2006/0084984 A1 | 4/2006 | Kim | |
| 2006/0084987 A1 | 4/2006 | Kim | |
| 2006/0095134 A1 | 5/2006 | Trieu et al. | |
| 2006/0129147 A1 | 6/2006 | Biedermann et al. | |
| 2006/0142758 A1 | 6/2006 | Petit | |
| 2006/0142760 A1 | 6/2006 | McDonnell | |
| 2006/0155279 A1 | 7/2006 | Ogilvie | |
| 2006/0184171 A1 | 8/2006 | Biedermann et al. | |

FOREIGN PATENT DOCUMENTS

| | | |
|---|---|---|
| GB | 2382304 | 5/2003 |
| WO | 01/45576 | 6/2001 |
| WO | 2005/112835 | 12/2005 |

OTHER PUBLICATIONS

Wang, A., et al. "Suitability and Limitations of Carbon Fiber Reinforced PEEK Composites as Bearing Surfaces for Total Joint Replacements," WEAR, 225-229, pp. 724-727 (1999).

Spinal System 510(k)s—Guidance for Industry and FDA Staff. www.fda.gov/cdrh/ode/guidance/636.html. Retrieved on Jul. 13, 2006.

Green, Stuart, "Using Implantable-Grade PEEK for In Vivo Devices," www.devicelink.com/mddi/archive/05/05/023.html. Retrieved on Jul. 13, 2006.

* cited by examiner

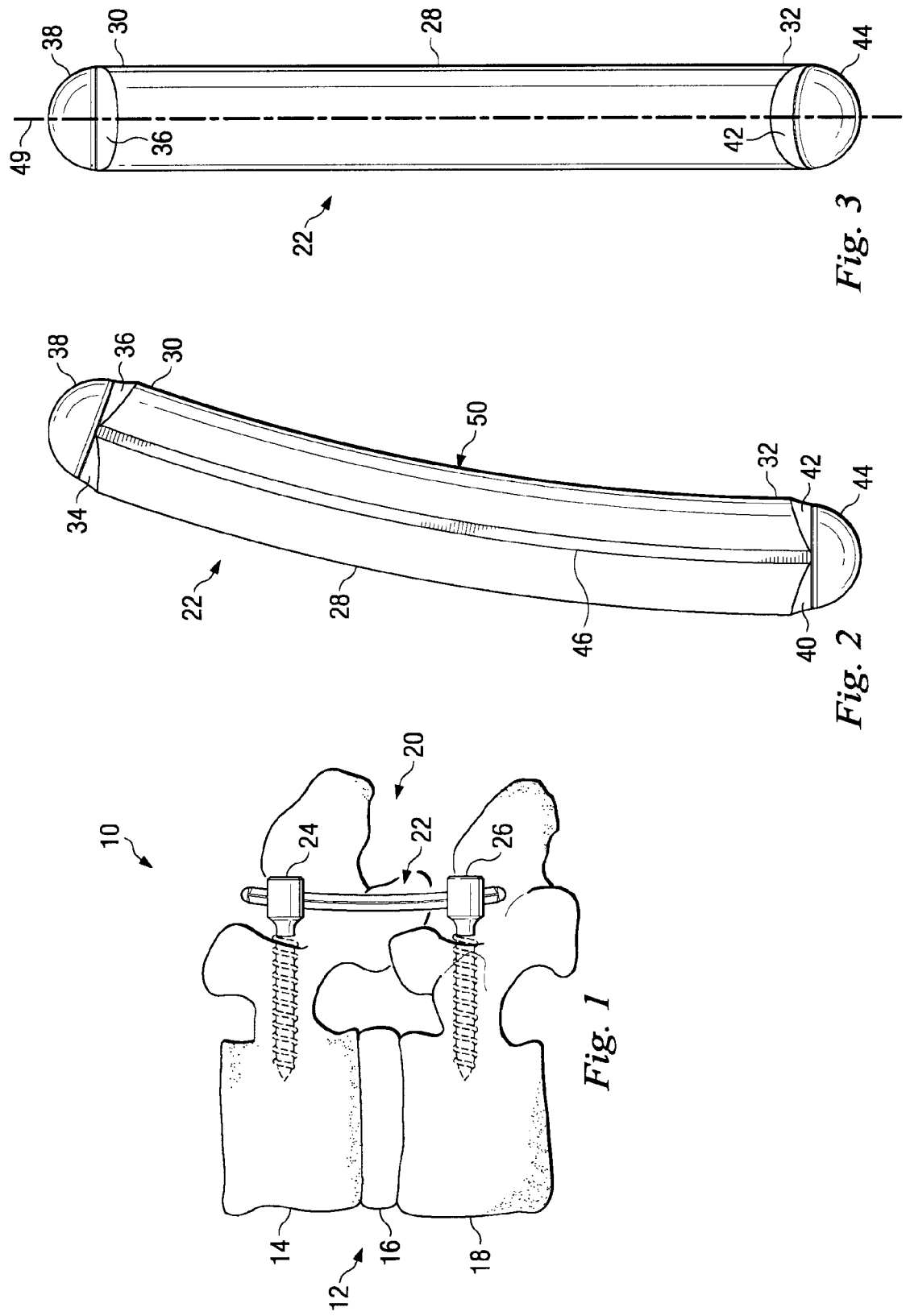

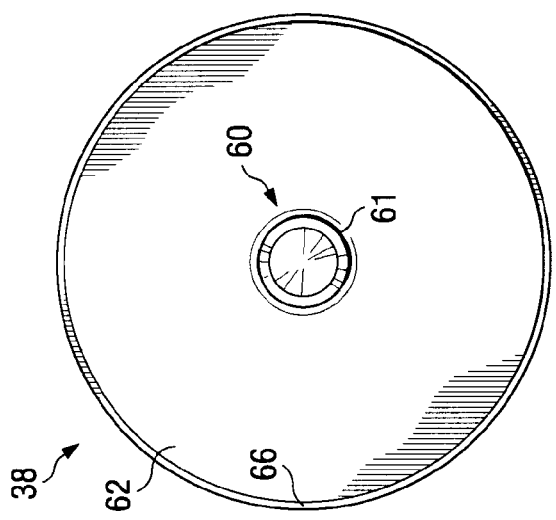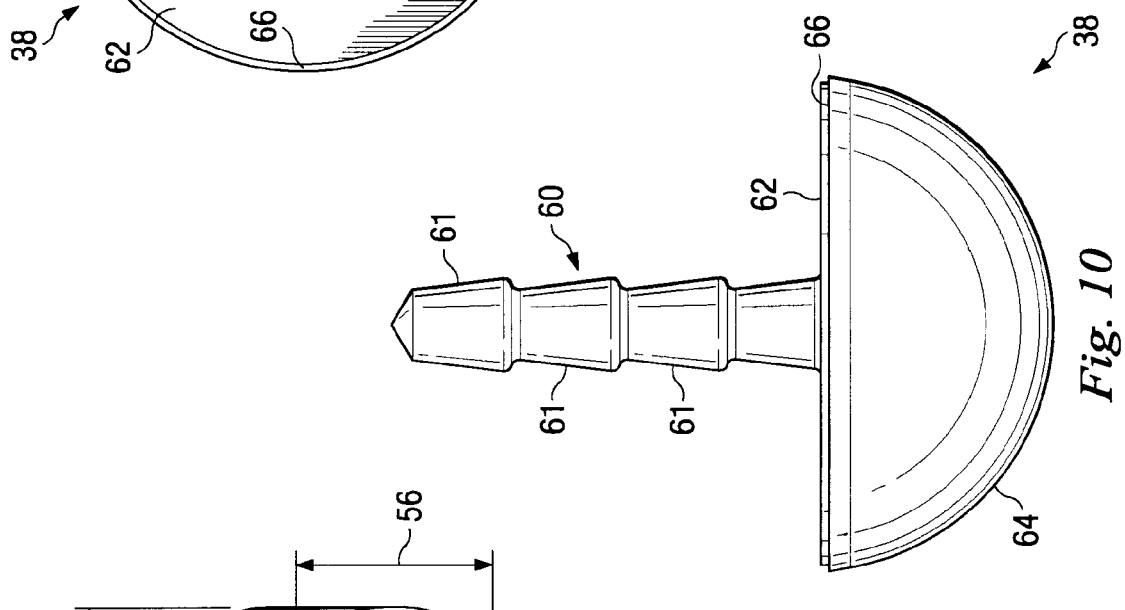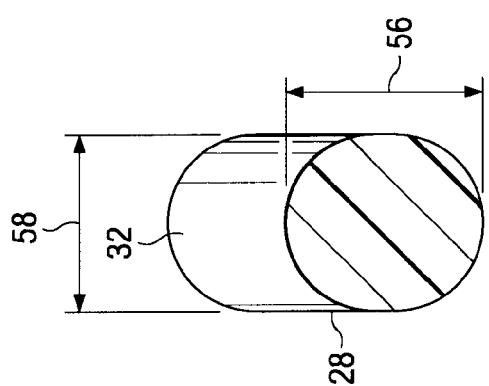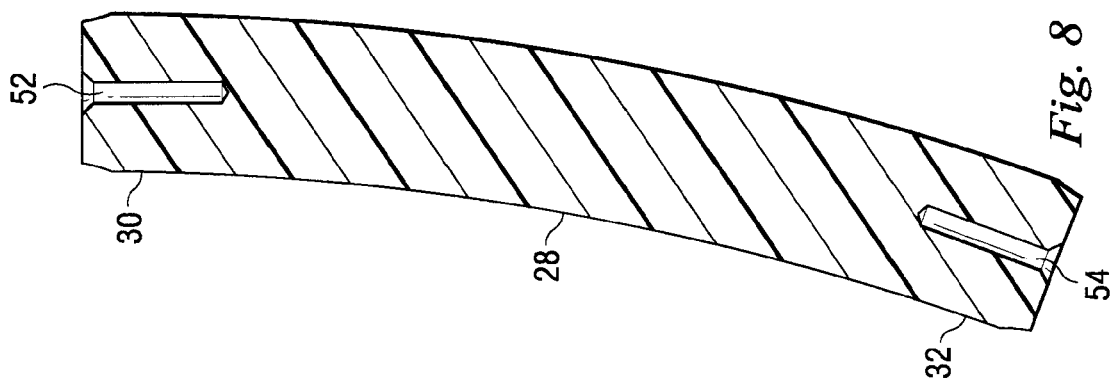

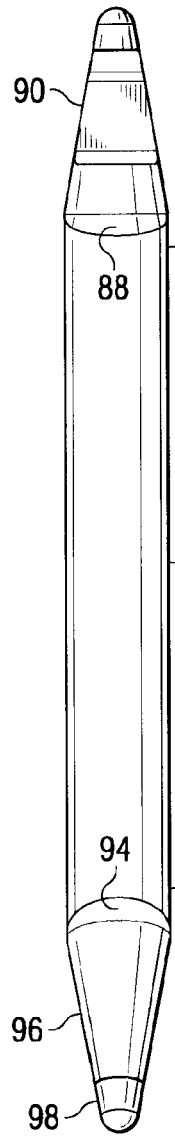 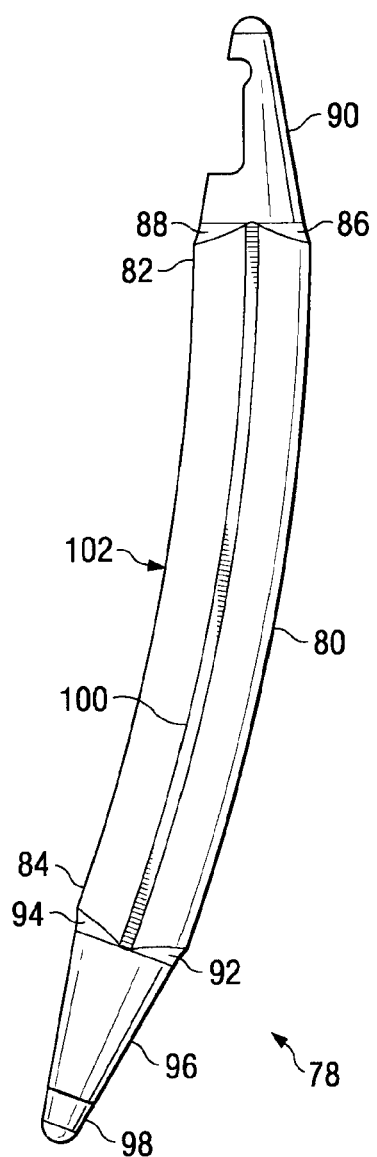 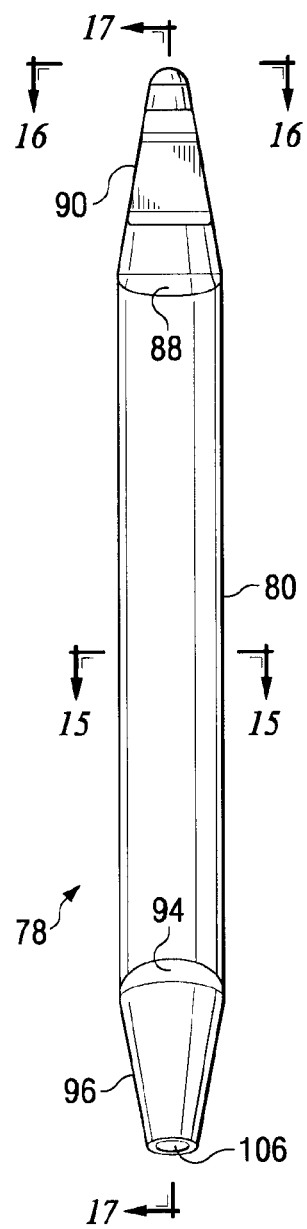
*Fig. 12*  *Fig. 13*  *Fig. 14*
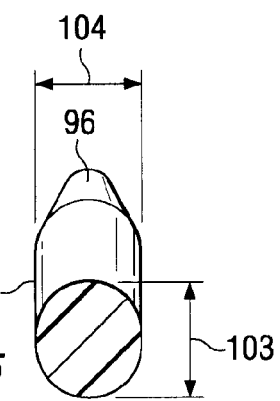 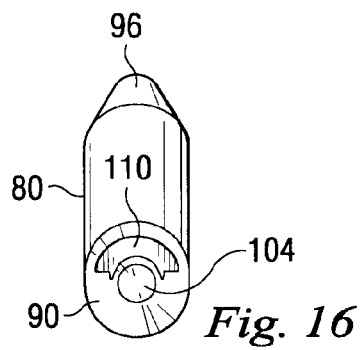
*Fig. 15*  *Fig. 16*

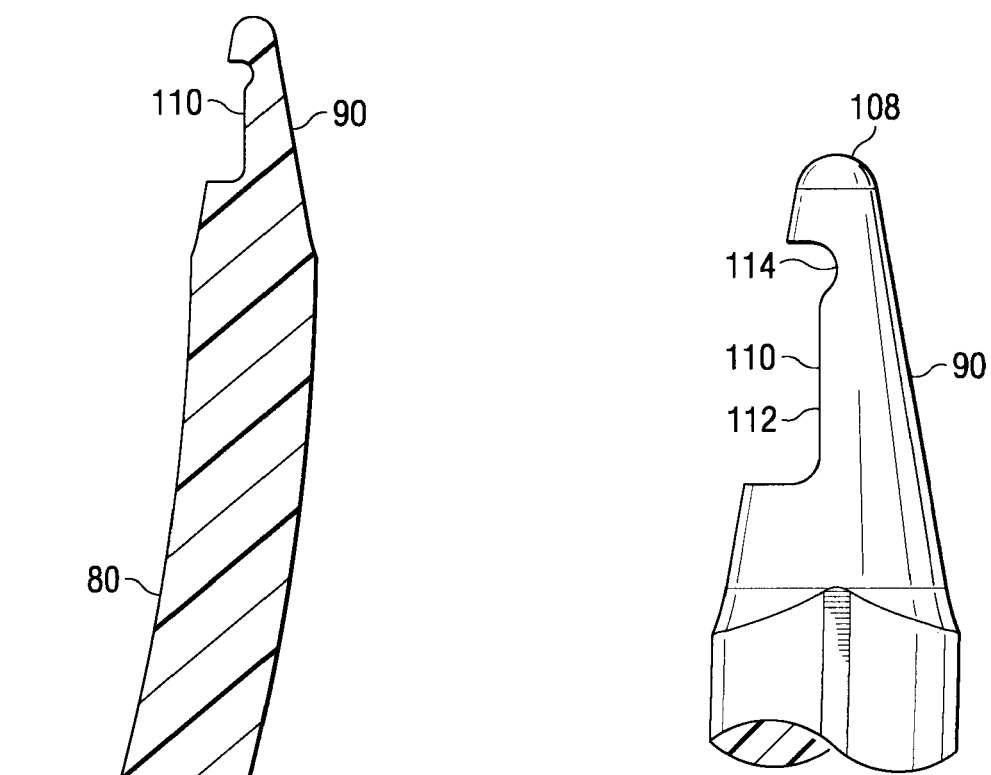
Fig. 17
Fig. 18
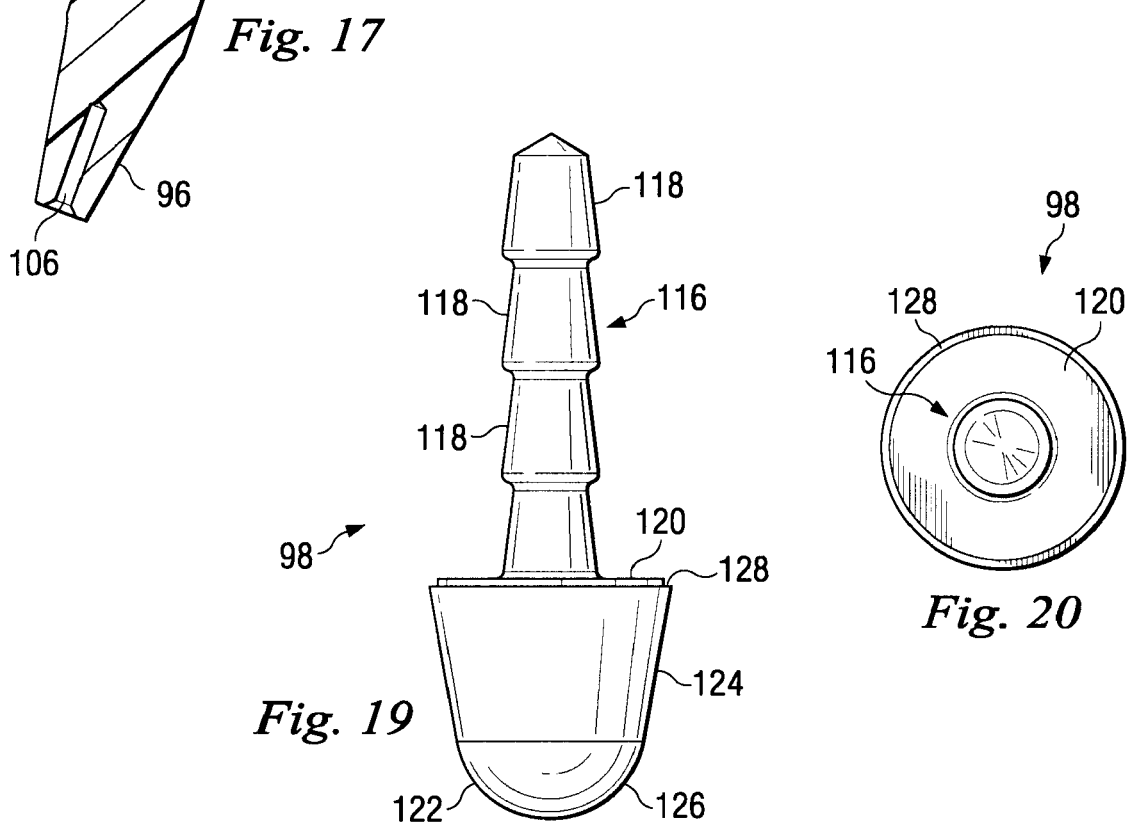
Fig. 19
Fig. 20

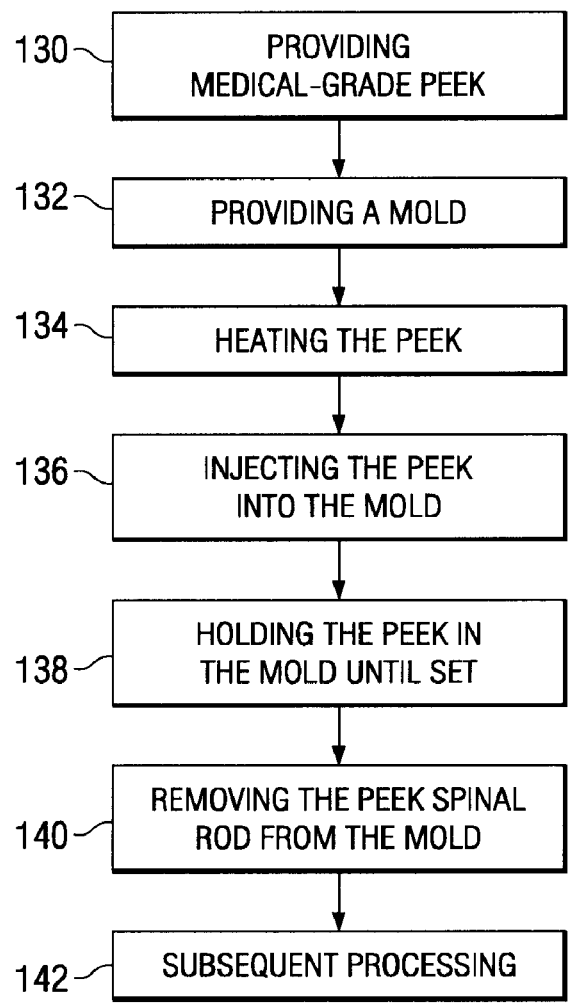
*Fig. 21*
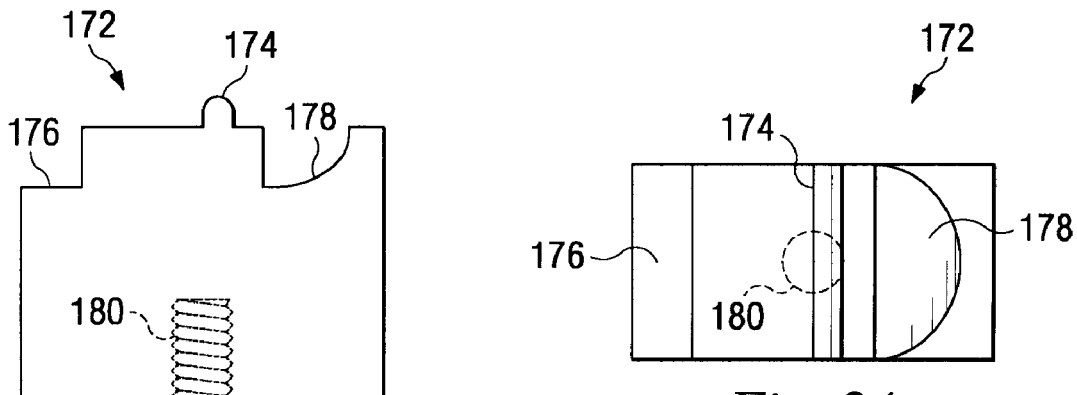
*Fig. 23*   *Fig. 24*

POLYMER RODS FOR SPINAL APPLICATIONS

TECHNICAL FIELD

Embodiments of the present disclosure relate generally to spinal rods and methods for manufacturing spinal rods. In some embodiments, the present disclosure relates to curved polyetheretherketone (PEEK) spinal rods and methods of manufacturing the rods via injection and compression molding.

BACKGROUND

Characteristics of implantable-grade or medical-grade polymers—such as biocompatibility, strength, flexibility, wear resistance, and radiolucence—make them especially suitable for use in medical device applications such as spinal implants and spinal rods. Although existing devices and methods utilizing polymers in these applications have been generally adequate for their intended purposes, they have not been entirely satisfactory in all respects.

SUMMARY

A method of manufacturing an elongated spinal fixation member is disclosed. In one embodiment, the method includes providing medical-grade polymer; providing a mold for creating a curved spinal fixation member; injecting the polymer into the mold until the mold is filled; holding the injected polymer in the mold until it sets; and removing the polymer from the mold. The method may include additional steps, such as preparing and drying the polymer.

In a second embodiment, a spinal rod is provided. The spinal rod includes an arcuate main body having a first end portion, a second end portion, and a central portion extending substantially between the first end portion and the second end portion. The central portion has an oblong cross-section with a height greater than its width. The first end portion has a substantially circular first end-portion surface and a first end-cap opening extending therethrough. The second end portion has a substantially circular second end-portion surface and a second end-cap opening extending therethrough. The arcuate main body is molded from a polymer. The spinal rod also includes a first end cap. The first end cap has a first projection adapted to mate with the first end-cap opening. The first end cap also has a tool engagement portion opposite the first projection. The tool engagement portion is adapted for engagement with a surgical instrument. The spinal rod also includes a second end cap. The second end cap has a second projection adapted to mate with the second end-cap opening. The second end cap also has a rounded end portion opposite the second projection.

In another embodiment, a spinal rod is provided. The spinal rod includes an arcuate main body having a first end portion, a second end portion, and a central portion extending substantially between the first end portion and the second end portion. The central portion has an oblong cross-section with a height greater than its width. The first end portion has a recess adapted for engagement with a surgical instrument. The second end portion has a substantially circular end-portion surface and an end-cap opening extending therethrough. The first and second end portions and the central portion of the arcuate main body are integrally formed of a polymer that is set into its final shape. The spinal rod also includes an end cap having a projection adapted to mate with the end-cap opening and having a rounded end portion opposite the projection.

Additional and alternative features, advantages, uses, and embodiments are set forth in or will be apparent from the following description, drawings, and claims.

BRIEF DESCRIPTION OF THE DRAWINGS

FIG. 1 is a diagrammatic side view of an arrangement that embodies aspects of the present disclosure.

FIG. 2 is a diagrammatic side view of a spinal rod of the arrangement of FIG. 1.

FIG. 3 is diagrammatic front view of the spinal rod of FIG. 2.

FIG. 8 is a sectional view of the portion of the spinal rod of FIG. 5 taken along line 8-8.

FIG. 9 is a sectional view of the portion of the spinal rod of FIG. 5 taken along line 9-9.

FIG. 10 is a diagrammatic side view of an end cap of the spinal rod of FIG. 2.

FIG. 11 is a diagrammatic end view of the end cap of FIG. 10.

FIG. 12 is a diagrammatic front view similar to FIG. 3, but showing an alternative embodiment.

FIG. 13 is a diagrammatic side view of the spinal rod of FIG. 12.

FIG. 14 is a diagrammatic front view of a portion of the spinal rod of FIG. 12.

FIG. 15 is a sectional view of the portion of the spinal rod of FIG. 14 taken along line 15-15.

FIG. 16 is a diagrammatic end view of the portion of the spinal rod of FIG. 14 taken along line 16-16.

FIG. 17 is a sectional view of the portion of the spinal rod of FIG. 14 taken along line 17-17.

FIG. 18 is a diagrammatic side view of one end of the portion of the spinal rod of FIG. 14.

FIG. 19 is a diagrammatic side view of an end cap of the spinal rod of FIG. 12.

FIG. 20 is a diagrammatic end view of the end cap of FIG. 19.

FIG. 21 is a flow-chart that embodies aspects of the present disclosure.

FIG. 23 is a diagrammatic side view of a end cap mold that embodies aspects of the present disclosure.

FIG. 24 is a diagrammatic top view of the end cap mold of FIG. 23.

DESCRIPTION

Figure 7:
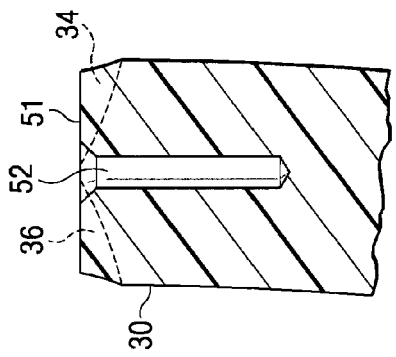
FIG. 7 is a diagrammatic, fragmentary side view of one end of the portion of the spinal rod of FIG. 5.

For the purpose of promoting an understanding of the principles of the invention, reference will now be made to the embodiments, or examples, illustrated in the drawings and specific language will be used to describe the embodiments. It will nevertheless be understood that no limitation of the scope of the invention is intended. Any alterations and further modifications of the described embodiments, and any further applications of the principles of the invention as described herein are contemplated as would normally occur to one skilled in the art to which the invention relates.

FIG. 1 is a diagrammatic side view of an arrangement 10 that embodies aspects of the present invention. The arrangement 10 includes a motion segment 12. The motion segment 12 includes a superior vertebra 14, an intervertebral disc 16, and an inferior vertebra 18. As shown in FIG. 1, in one embodiment the motion segment 12 is a segment of the lumbar spine. More particularly, the superior vertebra 14 and inferior vertebra 18 represent vertebrae L4 and L5, respectively.

The arrangement 10 also includes a spinal implant 20. The spinal implant 20 includes an elongated spinal fixation member or spinal rod 22 and fixation elements 24 and 26. The fixation element 24 secures the spinal rod 22 to the superior vertebra 14 and the fixation element 26 secures the spinal rod to the inferior vertebra 18. The spinal rod 22 is formed substantially of polymer material. The spinal rod 22 may be formed from any appropriate medical-grade polymer including, but not limited to members of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); cross-linked UHMWPE; and nano-material reinforced polymers.

Figure 4:
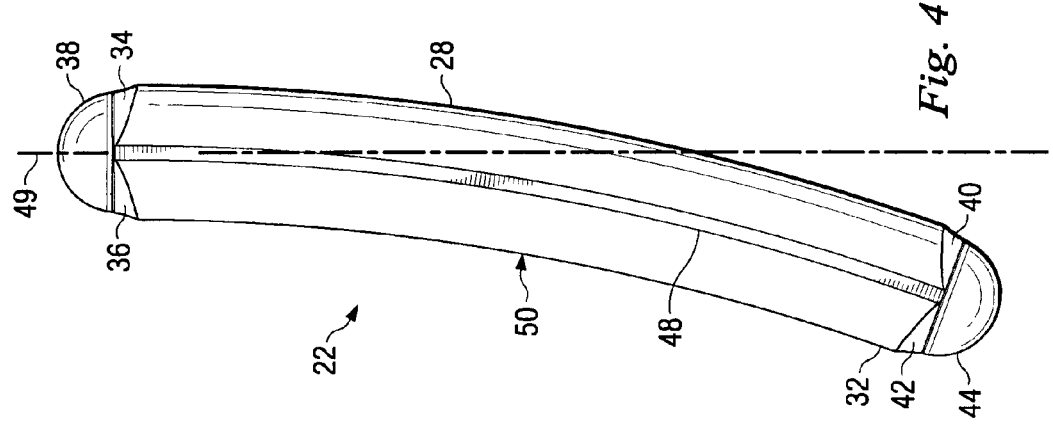
FIG. 4 is a diagrammatic side view of the spinal rod of FIG. 2.

FIGS. 2-4 illustrate various details of the spinal rod 22. FIG. 2 is a diagrammatic side view of the spinal rod 22. FIG. 3 is diagrammatic front view of the spinal rod 22. FIG. 4 is a diagrammatic side view of the spinal rod 22 opposite that of FIG. 2. Referring to FIGS. 2-4, the spinal rod 22 includes a body portion 28 that extends substantially along its length. The body portion 28 includes two end portions 30 and 32. The end portion 30 includes two external tapers 34 and 36. Further, the end portion 30 securely mates with an end cap 38. The end portion 32 is substantially similar to end portion 30. For example, the end portion 32 includes two external tapers 40 and 42 similar to tapered portions 34 and 36 and also mates with an end cap 44 similar to end cap 38. In some embodiments, the end portions 30 and 32 taper to a geometry to substantially match a geometry of a surface of the end caps 38 and 44.

The spinal rod 22 also includes markers 46 and 48 that extend along each of the sides of the main body 28. The markers 46 and 48 serve as visual guidance markers for the surgeon during surgery. The markers 46 and 48 provide the surgeon with an easily identifiable marking for orienting the spinal rod 22 during implantation and fixation. In one embodiment, the markers 46 and 48 appear shiny or polished in comparison to a duller texture of the main body 28. The markers 46 and 48 can be formed polishing a portion corresponding to the markers 46 and 48 of a mold used to form the rod 22, while the remainder of the mold is vapor-honed. The vapor-honed portions of the mold will create a dull finish or texture on the rod 22 that provides contrast to the shiny markers 46 and 48 created by the polished portion. In other embodiments, the markers are colored, etched, marked with a radiopaque ink, or otherwise treated to be visible against the main body 28. In some embodiments, a radiopaque pin is inserted through the rod to provide visualization using fluoroscopy. A plurality of radiopaque pins is used in other embodiments. The pins may be placed anywhere along the length of the rod. In some embodiments a single marker is used. Further, in some embodiments the markers are not lines extending along the sides of the rod, but are other shapes and designs for providing a visual guidance marker to a surgeon. The marker can also be placed anywhere on the rod, including the front, back, top, bottom, and sides.

The spinal rod 22 is curved along its length and has a radius of curvature 50, as shown in FIGS. 2 and 4. In the illustrated lumbar embodiment, the radius of curvature 50 is substantially uniform along the spinal rod 22 and has a length of 123.4 mm. As seen in FIGS. 3 and 4, the spinal rod 22 includes a longitudinal axis 49 extending substantially from end portion 30 to end portion 32. In the current embodiment, as the main body 28 extends from the end portion 30 towards the end portion 32 the main body curves away from the longitudinal axis 49, as best seen in FIG. 4. In other embodiments, the radius of curvature is between 50 mm and 200 mm. In yet other embodiments, the spinal rod has multiple radii of curvature along its length. Further, in some embodiments the spinal rod curves in multiple directions. For example, the rod may have multiple curves along its length to accommodate the transition between lumbar and thoracic curvatures, and between thoracic and cervical curvatures.

The actual structural design and radius of curvature of the spinal rod is tailored for the particular use of the spinal rod. In that regard, the spinal rod may be used in the cervical, thoracic, and lumbar regions of the spine and, in some embodiments, the spinal rod may extend across multiple regions of the spine. For example, the shape and the radius of curvature is adjusted to match the lordosis or kyphosis for the region of the spine where the spinal rod is to be implanted. For example, rods utilized to treat scoliosis may include curves extending in the anterior-posterior plane as well as in the medial-lateral plane. In a further embodiment, the elongated fixation member includes a rod portion and a plate portion joined to the rod portion. This may find application in joining the spine to the head. In still a further embodiment, the elongated fixation member is a curved plate having one or more holes extending therethrough adapted to receive bone engagement fasteners.

Figure 6:
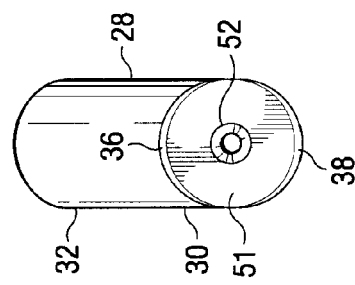
FIG. 6 is a diagrammatic end view of the portion of the spinal rod of FIG. 5 taken along line 6-6.
Figure 5:
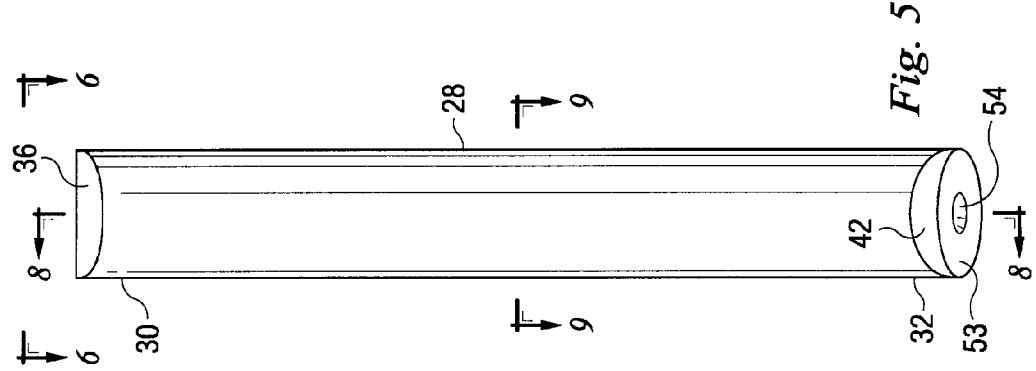
FIG. 5 is a diagrammatic front view of a portion of the spinal rod of FIG. 2.

FIGS. 5-9 illustrate additional details of the main body 28 of the spinal rod 22. FIG. 5 is a diagrammatic front view of the main body 28 of the spinal rod 22. FIG. 6 is a diagrammatic end view of the main body 28 shown in FIG. 5 taken along line 6-6. FIG. 7 is a diagrammatic, fragmentary side view of the end portion 30 of the main body 28. FIG. 8 is a sectional view of the main body 28 shown in FIG. 5 taken along line 8-8. FIG. 9 is a sectional view of the main body 28 shown in FIG. 5 taken along line 9-9.

Referring to FIGS. 5-9, the tapers 34 and 36 serve to transition the end portion 30 from an oblong cross-section of the main body 28 to a substantially cylindrical or circular cross-section at its end surface 51. An opening 52 is centrally located in the end surface 51 and extends into the end portion 30. The opening 52 is substantially cylindrical, but has a flared opening adjacent end surface 51 and a tapered ending as it extends towards the main body 28. The opening 52 is adapted to selectively receive end cap 38. Similarly, tapers 40 and 42 serve to transition the end portion 32 from the oblong cross-section of the main body 28 to a substantially cylindrical or circular cross-section at its end surface 53. An opening 54 is centrally located in the end surface 53 and extends into the end portion 32. The opening 54 is substantially similar to opening 52. That is, the opening 54 is substantially cylindrical, but has a flared opening adjacent end surface 53 and a tapered ending as it extends towards the main body 28. The opening 54 is adapted to selectively receive end cap 44.

As best seen in FIG. 9, the main body 28 has a non-circular cross-section having a height 56 and a width 58. In the illustrated embodiment the cross-sectional area is oval shaped. In the current embodiment, the main body 28 has a substantially uniform cross-section that extends substantially along its length with the height 56 being greater than the width 58. In other embodiments, the width is greater in the height. In yet other embodiments, the height and width are substantially equivalent such that the main body of the spinal rod has a substantially cylindrical or circular cross-section. In some embodiments, the height and width of the main body varies along the length of the spinal rod, such that the cross-section is not uniform. In that regard, the spinal rod can be considered a plate in some embodiments. In other embodiments, the spinal rod can be considered a plate-rod combination.

The cross-section of the main body is varied in some embodiments to obtain desired physical properties, such as the appropriate stiffness/flexibility and support strength. As with the radius of curvature and other features of the spinal rod, the cross-section is tailored for the particular use of the spinal rod. For example, the cross-section is configured to match the desired flexibility and support for the region of the spine where the spinal rod is to be implanted. For example, the superior portion of a spinal rod configured to extend between multiple vertebrae has a first cross-sectional area and the inferior portion has a second cross-sectional area, with the second cross-sectional area being greater than the first. Such a rod is useful in treating scoliosis or in dynamic stabilization of the spine. In other embodiments, the rod has additional cross-sectional areas with various combinations of larger, smaller, and different shaped cross-sections.

Further, as illustrated and described above, the spinal rod 22 is substantially symmetrical such that it may be used on both the left and right sides of the spine. In other embodiments, however, the spinal rod is designed for placement specifically on either the left or right side of the spine. The spinal rod can be tailored for placement on a particular side by changing the general shape, the radius of curvature, the cross-section, or other appropriate features of the spinal rod.

FIGS. 10 and 11 illustrate additional details of the end cap 38 of the spinal rod 22. The end cap 44 is substantially similar to the end cap 38 and, therefore, will not be described in detail. FIG. 10 is a diagrammatic side view of the end cap 38. FIG. 11 is a diagrammatic end view of the end cap 38. Referring to FIGS. 10 and 11, the end cap 38 includes a projection 60 for engaging the opening 52 in end portion 30 of the main body 28. The projection 60 is adapted to be press-fit into opening 52. In the current embodiment, the projection 60 includes tapered engagement portions 61. The narrow leading ends of the tapered engagement portions 61 facilitate insertion of the projection 60 into the opening 52 of the end portion 30. Once inserted, the wider trailing ends of the tapered engagement portions 61 prevent the end cap 38 from retracting or falling out of the opening 52.

The projection 60 is connected to a base 62. As best seen in FIG. 11, the projection 60 is centered on the base 62. The base 62 is circular and has a radius substantially similar to that of the end surface 51 of the end portion 30. Since the projection 60 is centrally located on the base 62, when the projection engages the opening 52 of the end portion 30 the base 62 and the end surface 51 are in substantial alignment. A cap 64 is connected to the base 62 opposite the projection 60. In the current embodiment, the cap 64 has a substantially spherical outer surface. A lip 66 of the cap 64 extends slightly beyond the base 62 so that the outer surface of the cap 64 substantially matches up with the outer surface of the end portion 30 when the projection 60 is engaged with the opening 52.

The end cap 38 is formed from an at least partially radiopaque material. In the current embodiment the end cap is formed from a metal, and in particular titanium. Being radiopaque allows the end cap 38 to be seen using fluoroscopy. This provides the surgeon with an accurate means for tracking the spinal rod 22 in embodiments where the main body 28 is formed of radiolucent material. In other embodiments, the end cap 38 is formed from other suitable biocompatible materials including metals, ceramics, polymers, and combinations thereof. For example, in some embodiments metals such as cobalt-chromium alloys, titanium alloys, nickel titanium alloys, and stainless steel alloys are suitable. In other embodiments, ceramic materials such as aluminum oxide or alumina, zirconium oxide or zirconia, compact of particulate diamond, or pyrolytic carbon are suitable. In yet other embodiments polymer materials are used, including members of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and cross-linked UHMWPE. In some embodiments, the end cap 38 is substantially radiolucent. Where the end cap 38 is substantially radiolucent, it may include a radiopaque marker therein.

FIG. 12 is a diagrammatic front view similar to FIG. 3, but showing an alternative embodiment of a spinal rod 78. FIG. 13 is a diagrammatic side view of the spinal rod 78. Referring to FIGS. 12 and 13, the spinal rod 78 includes a body portion 80 that extends substantially along its length. The body portion 80 includes two end portions 82 and 84. The end portion 82 includes two tapers 86 and 88. Integrally formed to the end portion 82 is an end cap 90. The end cap 90 is adapted for selective engagement with a surgical instrument. The end portion 84 includes two tapers 92 and 94 and is integrally formed with a tip portion 96. The tip portion 96 is tapered and substantially conical in shape. The tip portion 96 of the end portion 84 securely mates with an end cap 98.

The spinal rod 78 includes a marker 100 extending along one side of the main body 80. As previously described, the marker 100 serves as a visual guidance marker for the surgeon during surgery. The marker 100 provides the surgeon with an easily identifiable marking for orienting the spinal rod 78 during implantation and fixation.

The spinal rod 78 is curved along its length and has a radius of curvature 102, as shown in FIG. 13. In the current embodiment, the radius of curvature 102 is substantially uniform along the length of the spinal rod 78.

FIGS. 14-18 illustrate additional details of the integrally formed portions of the spinal rod 78. FIG. 14 is a diagrammatic front view of the integrally formed portions of the spinal rod 78. FIG. 15 is a sectional view of the portions of the spinal rod 78 of FIG. 14 taken along line 15-15. FIG. 16 is a diagrammatic end view of the portions of the spinal rod 78 of FIG. 14 taken along line 16-16. FIG. 17 is a sectional view of the portions of the spinal rod 78 of FIG. 14 taken along line 17-17. FIG. 18 is a diagrammatic side view of the end cap 90 of the spinal rod 78.

As best seen in FIG. 15, the main body 80 has an oblong cross-section having a height 103 and a width 104. In the current embodiment, the main body 80 has a substantially uniform cross-section that extends substantially along its length with the height 103 being greater than the width 104. Referring to FIGS. 14-18, the tapers 92 and 94 serve to transition the end portion 84 from the oblong cross-section of the main body 80 to a substantially circular cross-section of the tip portion 96 and an end surface 103. An opening 104 is centrally located in the end surface 103 and extends into the end portion 84. The opening 104 is substantially cylindrical, but has a flared opening adjacent end surface 103 and a tapered ending within the tip portion 96. The opening 104 is adapted to selectively receive end cap 98.

The end cap 90 is adapted for engagement with a surgical instrument. To that end, the end cap 90 includes a rounded tip 108 and a recess 110. In the current embodiment, the recess 110 includes a substantially flat portion 112 and a depression 114. In other embodiments, the end cap 90 includes other features to facilitate engagement with a surgical instrument. For example, the end cap includes recesses, projections, surface textures, and threading in some embodiments.

FIG. 19 is a diagrammatic side view of the end cap 98. FIG. 20 is a diagrammatic end view of the end cap 98. Referring to FIGS. 19 and 20, the end cap 98 includes a projection 116 for engaging the opening 106 in tip portion 96. The projection 116 is adapted to be press-fit into the opening 106. The projection 116 includes tapered engagement portions 118. The narrow leading ends of the tapered engagement portions 118 facilitate insertion of the projection 116 into the opening 106 of the tip portion 96. Once inserted, the wider trailing ends of the tapered engagement portions 118 prevent the end cap 98 from retracting or falling out of the opening 106.

The projection 116 is connected to a base 120. As best seen in FIG. 20, the projection 116 is centered on the base 120. The base 120 is circular and has a radius substantially similar to that of the end surface 105. Since the projection 116 is centrally located on the base 120, when the projection engages the opening 106 the base 120 will be in substantial alignment with the end surface 105. A cap 122 is connected to the base 120 opposite the projection 116. In the current embodiment, the cap 122 has a tapered, conical portion 124 and a rounded end portion 126. A lip 128 of the cap 122 extends from the conical portion 124 slightly beyond the base 120 so that the outer surface of the cap 122 substantially matches up with the outer surface of the tip portion 96 when the projection 116 is engaged with the opening 106. In some embodiments the cap 122 is shaped to facilitate insertion of the spinal rod 78 by facilitating displacement of a tissue without damaging the tissue. In one such embodiment, the cap 122 includes the rounded end portion 126.

The curved spinal rods disclosed above and other curved spinal rods may be manufactured out of polyetheretherketone (PEEK) using the following devices and methods. For the sake of clarity and without limitation, specific references will be made to manufacturing the various features and components of the spinal rod 78 disclosed above. It should be recognized that similar techniques and methods are used for forming other spinal rods.

FIG. 21 is a flow-chart illustrating a method of manufacturing spinal rods that embodies aspects of the present disclosure. The method includes providing medical-grade polyetheretherketone (PEEK) 130; providing a mold shaped for creating a curved spinal rod 132; heating the PEEK 134; injecting the PEEK into the mold 136; holding the injected PEEK in the mold until it sets 138; removing the PEEK from the mold 140; and subsequent processing 142. The method can also include preparing and drying the PEEK.

With respect to providing the PEEK 130, medical-grade PEEK is used to form the spinal rods. Medical-grade PEEK is available in various compounds, viscosities, and with various additives. For example, PEEK is available with additives such as carbon fiber and barium sulfate. The additives are used to change the physical properties of the PEEK, such as tensile strength and radiopacity. Similarly, PEEK is available in regular viscosity, high viscosity, and low viscosity. The use of high viscosity PEEK is advantageous where, for example, the spinal rod is likely to bear heavy loads. The use of low viscosity PEEK is advantageous where the spinal rod is to be flexible, have a thin cross-section, and other applicable situations. Medical-grade PEEK is commercially available from Invibio Biomaterial Solutions of Lancashire, UK under the trade-name PEEK-OPTIMA™. Normal viscosity PEEK-OPTIMA™ is available under as product number LT1; lower viscosity PEEK-OPTIMA™ is available as product number LT2; and even lower viscosity PEEK-OPTIMA™ is available as product number LT3. The actual properties of the PEEK material chosen can affect the desired temperature and pressure parameters for the method. For illustration purposes and without limitation, the method described herein may utilize regular viscosity PEEK-OPTIMA™ (LT1).

In other embodiments, polymers other than the various PEEK compounds may be used. For example, suitable polymers include members of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); cross-linked UHMWPE; and nano-material reinforced polymers. The actual properties of the polymer material chosen can affect the desired temperature and pressure parameters for the method.

Figure 22:
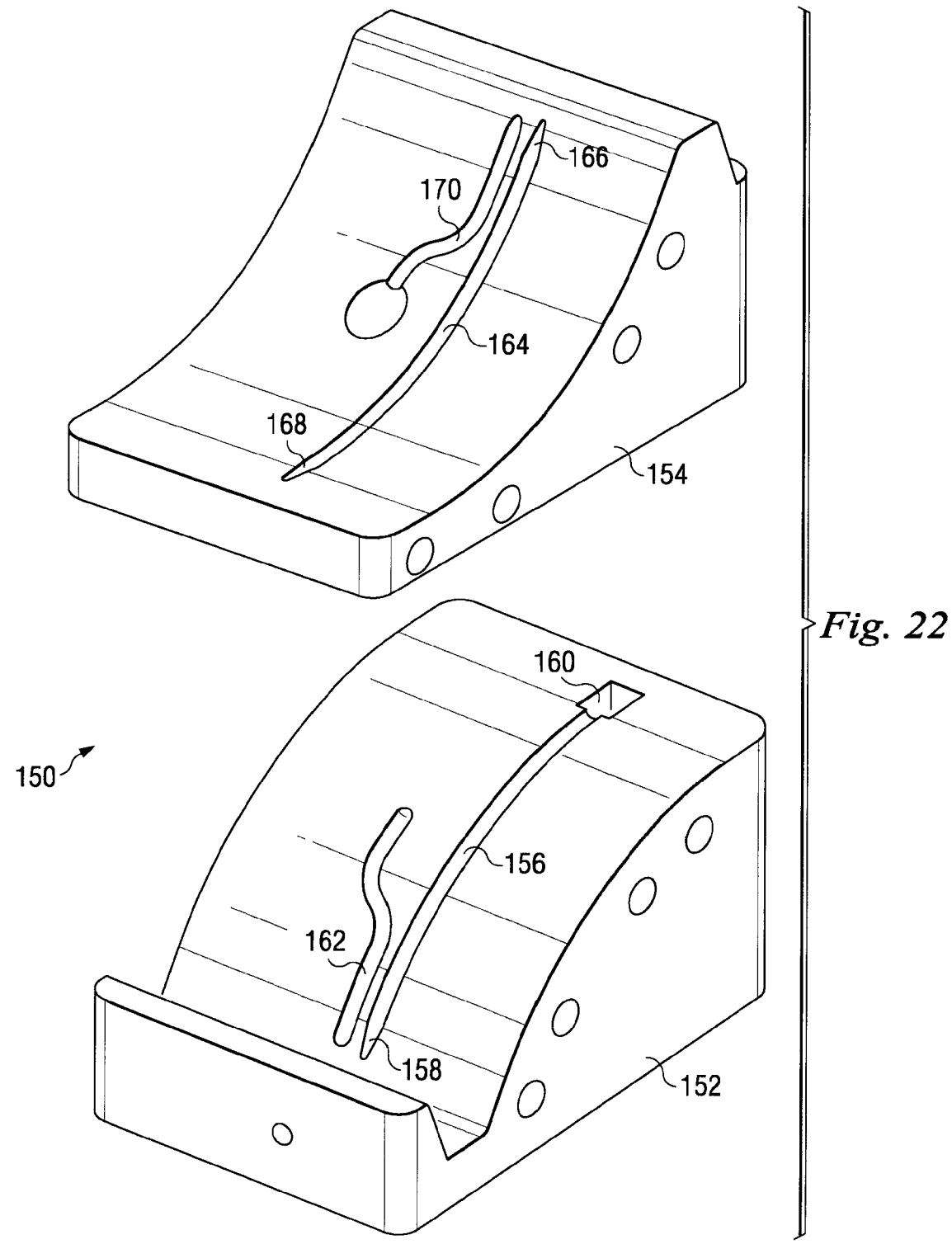
FIG. 22 is a diagrammatic perspective view of a spinal rod mold that embodies aspects of the present disclosure.

With respect to providing the mold 132, FIG. 22 is a diagrammatic perspective view of a spinal rod mold 150 that embodies aspects of the present disclosure. The mold 150 is adapted for use in the injection molding and compression molding of PEEK into curved spinal rods. As such, the mold 150 is configured for use with and in other machinery and is able to withstand the high temperatures and high pressures of the manufacturing process. The mold 150 includes a lower piece 152 and an upper piece 154. In use, the upper piece 154 is securely fitted to the lower piece 152. The seal between the upper and lower pieces 154 and 152 must be sufficiently tight to prevent PEEK from escaping the mold even at the high temperatures and pressures of the manufacturing process.

The lower piece 152 includes a main recess 156, a tip recess 158, an end cap opening 160, and a runner recess 162. The end cap opening 160 is adapted to receive one of a plurality of end cap molds. One example of an end cap mold is provided in FIGS. 23 and 24. FIG. 23 is a diagrammatic side view of a end cap mold 172. FIG. 24 is a diagrammatic top view of the end cap mold 172. The end cap mold 172 is sized to mate with the end cap opening 160 of the lower piece 152. In the current embodiment, the end cap mold 172 includes a projection 174 and two recesses 176 and 178 for molding the shape of an end cap. In other embodiments, the end cap mold 172 include any number of projections, recesses, shapes, and textures for molding the end cap. Further, the end cap mold 172 includes an engagement mechanism 180. The engagement mechanism 180 is adapted to facilitate secure engagement of the end cap mold 172 to the lower piece 152. In the current embodiment, the engagement mechanism 180 is a threaded opening adapted to receive threaded member (e.g., a screw) that will securely engage the end cap mold 172 and the lower piece 152. The engagement mechanism 180 can take any form capable of helping to secure the end cap mold 172 to the lower piece 152. In some embodiments, the end cap mold 172 does not have an engagement mechanism 180.

The interchangeability of end cap molds within the end cap opening 160 allows the spinal rod 78 to be formed with various features on the end cap 90. For example, each of the plurality of end cap molds can be shaped for forming the end cap 90 to mate with a specific surgical instrument that the spinal rod 78 will be used with during implantation in the body. In other embodiments, the end cap opening 160 is itself a recess for shaping the end cap 90 of the spinal rod 78. The upper piece 154 includes a main recess 164, a tip recess 166, an end cap recess 168, and a runner recess 170. In other embodiments, the end cap recess 168 is replaced with an end cap opening similar to end cap opening 160 of the lower piece 152.

When fitted together the corresponding recesses of the upper and lower pieces 154 and 152 match up. For example, the main recesses 156 and 164 match up to form a recess to shape the body portion 80 of the spinal rod 78; the tip recesses 158 and 166 align to form a recess to shape the tip portion 96 of spinal rod 78; and the end cap opening 160 filled with an end cap mold will match up with the end cap recess 168 to form the opening to shape the end cap 90. Further, the runner recesses 162 and 170 will align. As described below, the runner recesses 162 and 170 receive the excess PEEK from the manufacturing process.

As mentioned previously, the precise shapes, curves, and cross-sections of the spinal rod 78 are configured for the specific application of the spinal rod. To that end, the main recesses 156 and 164 of the mold are shaped to form the desired shapes, curves, and cross-sections. Similarly, the other portions of the mold 150 such as the tip portions 158 and 166, and the end cap mold and end cap recess 168 are shaped for the desired features of these parts of the spinal rod. Further, the mold may include features for creating the visual markers of the rod. For example, in some embodiments the mold includes projections or recesses for creating a corresponding visual marker in the rod. In some embodiments portions of the mold have a textured surface, while other portions of the mold have a smooth surface, which causes the rod to have corresponding textured and smooth surfaces. The resulting contrast between the roughened or textured surface and the smooth or mirrored surface of the rod can be used as a visual marker.

With respect to heating the PEEK 134, the PEEK is heated at a temperature range between 600° and 800° Fahrenheit. More particularly, in one embodiment regular viscosity PEEK-OPTIMA™ (LT1) is melted at a temperature between 650° and 720° Fahrenheit. In embodiments utilizing complex geometries or large cross-sections, increasing the melting temperature to greater than 720° Fahrenheit allows the material to flow easier into the mold and fully fill the mold. Higher temperatures are also used when using various materials, such as impregnated PEEK polymers.

Once heated, the PEEK can be injected into the mold 136. The PEEK is injected at a temperature between 300° and 500° Fahrenheit. Further, the melted PEEK is injected with a pressure range between 5,000 and 15,000 psi. More particularly, in some embodiments the pressure range is between 10,000 and 13,000 psi. PEEK is inserted into the mold until the main recesses 156 and 164, tip recesses 158 and 166, and the end cap mold/recess 168 are completely filled. Once filled, any excess PEEK will flow into the runner recesses 162 and 170. When the portions of the mold for forming the spinal rod 78 are completely filled, the PEEK will have a peak pressure between 15,000 and 25,000 psi. More particularly, in some embodiments the peak pressure is between 19,000 and 23,000 psi. Further, when filled the back pressure of the PEEK is in a range between 500 and 1,500 psi.

Once the mold 150 is filled with melted PEEK to the appropriate level, the injected PEEK is held in the mold until the PEEK sets. The hold pressure or packing pressure can be in a range between 5,000 and 25,000 psi. More particularly, in some embodiments the hold pressure is between 18,000 and 23,000 psi. Further, in some embodiments the hold pressure is determined by decreasing the pressure approximately 200 psi from the peak pressure. The PEEK is maintained in the mold until it is substantially set.

After the PEEK is set, it can be removed from the mold 150. Where excess PEEK has flowed into the runner recesses of the mold, the runner will extend from the spinal rod. In these situations, the runner is removed from the spinal rod. Once the runner is removed, the spinal rod is subjected to additional processing. However, in some embodiments, no additional processing is performed on the spinal rod. That is, once the runner is removed the spinal rod is in its final, useable form.

The PEEK spinal rod removed from the mold 150 can be subjected various types of additional processing. For example, in some embodiments end caps, such as end caps 38 and 44 of spinal rod 22, are attached to the spinal rod. Where the spinal rod is not molded to include the appropriate openings for receiving the end caps, the openings are prepared. The openings are prepared by various methods including drilling, machining, or other suitable methods. Once the openings are prepared the end caps may be inserted into the openings. In some embodiments—especially where metal end caps are used—the end caps heat-staked to the PEEK rod. That is, the end caps are heated to approximately 400° Fahrenheit, or other appropriate temperature, prior to insertion into the openings. Heating the end caps causes the PEEK immediately surrounding the heated projection of end cap to conform to the contours of the end cap to further secure the end cap to the main body of the spinal rod. In other embodiments, the end cap 38 is heated after insertion into the opening 52. In yet other embodiments, the end cap 38 is inserted into the opening 52 and then blasted with an ultra-sonic horn to further secure the end cap to the main body 28.

In addition to attaching end caps, the spinal rod is subjected to other processing in some embodiments. For example, in some embodiments markers are added to the spinal rod to provide visual guidance markers. The markers can be added by vapor-honing, polishing, laser etching, or other appropriate methods. In some embodiments, length of the spinal rod is cut to length after removal from the mold. In some embodiments, the uncut PEEK rod has a length between 25 and 130 mm. The rod can be cut to virtually any appropriate length. Once cut to the appropriate length, other processing such as preparing the end portions to receive the end caps can be performed. In some embodiment, the spinal rod is modular such that a plurality of spinal rod components are connected together to form a single spinal rod of a desired length. Where the spinal rod is modular pieces can be added or removed to obtain the desired length.

In some embodiments, the rod is molded in multiple phases. For example, an upper section, a middle section, and a lower section of the rod can each be formed separately. Each section can have a different curvature. Each section can be formed of a different material, giving the rod different material properties in each section of the rod. For example, for patients that are still growing the section of the rod that is to be placed adjacent the apical portion of the spin could be formed of a stiffer material than the portions above and below it. Such an approach would allow for correction and stabilization of the spine. Further, the rod can be formed in multiple phases to create different geometries, such as a plate portion in combination with a rod portion. In that regard, the rod may molded to be combined with, mate with, or engage with other fixation devices, such as spinal plates.

Further, in at least one aspect the method of molding the rod described above is one exemplary embodiment of a method of forming a spinal rod where the rod is set in its final form. That is, the rod does not require additional processing, such as machining, after it is set. In other embodiments, the rod is set in its final form by other methods. For example, in one embodiment, the rod is formed by extruding the material into a desired shape and then setting the extruded material in the final shape. In another embodiment, the rod is formed by heating the polymer, bending or shaping the heated polymer into the desired shape, and cooling the polymer to set the shape into the final form. In other embodiments, the rod is subjected to additional processing, such as machining to modify the external dimensions to achieve a final form, after being set.

Other modifications of the present disclosure would be apparent to one skilled in the art. Accordingly, all such modifications and alternatives are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. An elongated spinal fixation member comprising:
an arcuate main body having a first end portion, a second end portion, and an elongated central portion extending substantially between the first end portion and the second end portion, the arcuate main body curved along its length between the first end portion and the second end portion;
the central portion having a substantially uniform oblong cross-section extending substantially along a length of the central portion, the cross-section having a height greater than a width as viewed in a plane generally perpendicular to the length of the central portion,
the first end portion having a substantially circular first end-portion surface and a first end-cap opening extending therethrough, the first end portion having at least one external taper transitioning the first end portion from the oblong cross-section of the central portion to the substantially circular first end-portion surface, the at least one external taper of the first end portion tapering more relative to the height of the central portion as compared to the width of the central portion;
the second end portion having a substantially circular second end-portion surface and a second end-cap opening extending therethrough, the second end-cap opening spaced from the first end-cap opening of the first end portion, the second end portion having at least one external taper transitioning the second end portion from the oblong cross-section of the central portion to the substantially circular first end-portion surface, the at least one external taper of the second end portion tapering more relative to the height of the central portion as compared to the width of the central portion;
wherein the arcuate main body is formed of a medical grade polymer and is set in its final form;
a first end cap having a first projection fixedly engaged with the first end-cap opening; and
a second end cap having a second projection fixedly engaged with the second end-cap opening and having a rounded end portion opposite the second projection, the second projection spaced from the first projection.

2. The elongated spinal fixation member of claim 1 wherein the first end cap is formed of a metal.

3. The elongated spinal fixation member of claim 2 wherein the second end cap is formed of a metal.

4. The elongated spinal fixation member of claim 3 wherein the first and second end caps are formed of a metal selected from the group consisting of titanium alloys, cobalt-chromium alloys, nickel titanium alloys, and stainless steel alloys.

5. The elongated spinal fixation member of claim 1 wherein the central portion includes a visual guidance marker thereon.

6. The elongated spinal fixation member of claim 5 wherein the visual guidance marker is a visible line on the central portion.

7. The elongated spinal fixation member of claim 1 wherein the rounded end portion of the second end cap is shaped to facilitate displacement of a tissue without damaging the tissue during insertion of the spinal rod.

8. The elongated spinal fixation member of claim 1 wherein the arcuate main body has a radius of curvature that is substantially uniform along its length.

9. The elongated spinal fixation member of claim 8 wherein the radius of curvature is approximately 123.4 mm.

10. The elongated spinal fixation member of claim 1, wherein the medical grade polymer is PEEK.

11. The elongated spinal fixation member of claim 10, wherein at least the arcuate main body is injection molded.

12. The elongated spinal fixation member of claim 1, wherein the first projection of the first end cap extends from a base portion of the first end cap, and wherein the first end cap includes a lip portion extending radially beyond the base portion such that an outer surface of the first end cap substantially matches up with the outer surface of the first end portion when the first projection is engaged with the first end-cap opening.

13. An elongated spinal fixation member comprising:
an arcuate main body having a first end portion, a second end portion, and an elongated central portion extending substantially between the first end portion and the second end portion, the central portion having a length extending along an arc between the first end portion and the second end portion, the central portion having an oblong cross-section with a height greater than a width as viewed in a plane extending perpendicular to the arc of the central portion, the oblong cross-section being substantially uniform along the length of the central portion, the first end portion having a recess, the second end portion having a substantially circular end-portion surface and an end-cap opening extending therethrough, wherein the first and second end portions and the central portion of the arcuate main body are integrally formed of a medical grade polymer and set in their final shape, wherein the arcuate main body comprises an external taper transitioning between the oblong cross-section of the central portion and the substantially circular end-portion surface of the second end portion, the external taper having a greater amount of taper relative to the height of the oblong cross-section as compared to the width of the oblong cross-section; and
an end cap having a projection adapted to mate with the end-cap opening and having a rounded end portion opposite the projection.

14. The elongated spinal fixation member of claim 13 wherein the main body is substantially radiolucent.

15. The elongated spinal fixation member of claim 14 wherein the end cap is substantially radiopaque.

16. The elongated spinal fixation member of claim 13, wherein a first portion of an outer surface of the arcuate main body has a first texture and a second portion of the outer surface has a second texture visually distinguishable from the first texture such that at least one of the first and second portions defines a visual guidance marker.

17. The elongated spinal fixation member of claim 16, wherein the first texture is roughened and the second texture is polished.

18. The elongated spinal fixation member of claim 17, wherein the visual guidance marker extends along the length of the central portion and along a lateral side of the arcuate main body.

19. The elongated spinal fixation member of claim 16, wherein the first projection of the first end cap is press-fit into the first end-cap opening.

20. The elongated spinal fixation member of claim 19, wherein the first projection comprises a plurality of tapered engagement portions such that leading sections of the tapered engagement portions facilitate insertion of the first projection into the first end-cap opening and trailing sections of the tapered engagement portions having a larger profile than the leading section prevent retraction of the first projection from the first end-cap opening.

21. The elongated spinal fixation member of claim 13, wherein at least the arcuate main body is injection molded.

22. The elongated spinal fixation member of claim 21, wherein a first portion of an outer surface of the arcuate main body has a first texture and a second portion of the outer surface has a second texture visually distinguishable from the first texture such that at least one of the first and second portions defines a visual guidance marker.

23. The elongated spinal fixation member of claim 22, wherein the first texture is roughened and the second texture is polished, and wherein the visual guidance marker extends substantially along the length of the central portion and along a lateral side of the arcuate main body.

24. The elongated spinal fixation member of claim 21, wherein the projection of the end cap is press-fit into the end-cap opening for fixed engagement with arcuate main body.

25. The elongated spinal fixation member of claim 24, wherein the projection comprises a plurality of tapered engagement portions such that leading sections of the tapered engagement portions facilitate insertion of the projection into the end-cap opening and trailing sections of the tapered engagement portions having a larger profile than the leading section prevent retraction of the projection from the end-cap opening.

* * * * *